United States Patent
Kobayashi et al.

(10) Patent No.: US 10,052,503 B2
(45) Date of Patent: *Aug. 21, 2018

(54) FIRST AGENT FOR OXIDATIVE HAIR DYE AND METHOD FOR STABILIZING COLOR TONE OF OXIDATIVE HAIR DYE COMPOSITION

(71) Applicant: HOYU CO., LTD., Nagoya-shi, Aichi-ken (JP)

(72) Inventors: Yosuke Kobayashi, Aichi-ken (JP); Yohei Mizukami, Aichi-ken (JP); Kohei Moriguchi, Aichi-ken (JP)

(73) Assignee: HOYU CO., LTD., Nagoya-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/649,866

(22) Filed: Jul. 14, 2017

(65) Prior Publication Data

US 2018/0021600 A1    Jan. 25, 2018

(30) Foreign Application Priority Data

Jul. 22, 2016   (JP) ................. 2016-144898

(51) Int. Cl.
| | |
|---|---|
| *A61Q 5/10* | (2006.01) |
| *A61K 8/41* | (2006.01) |
| *A61K 8/49* | (2006.01) |
| *A61K 8/34* | (2006.01) |
| *A61Q 5/08* | (2006.01) |

(52) U.S. Cl.
CPC ............... *A61Q 5/10* (2013.01); *A61K 8/347* (2013.01); *A61K 8/41* (2013.01); *A61K 8/411* (2013.01); *A61K 8/415* (2013.01); *A61K 8/49* (2013.01); *A61Q 5/08* (2013.01)

(58) Field of Classification Search
CPC . A61Q 5/10; A61K 8/415; A61K 8/49; A61K 2800/4324
See application file for complete search history.

(56) References Cited

U.S. PATENT DOCUMENTS

| | | | |
|---|---|---|---|
| 5,143,518 A | 9/1992 | Madrange | |
| 2004/0083557 A1* | 5/2004 | Au | ............... A61K 8/40 8/405 |
| 2011/0271466 A1* | 11/2011 | Ito | ............... A61K 8/347 8/408 |

FOREIGN PATENT DOCUMENTS

| | | |
|---|---|---|
| EP | 2609907 A1 | 7/2013 |
| JP | 2004-026834 A | 1/2004 |
| JP | 2016-132662 A | 7/2017 |
| WO | 99/36047 A | 7/1999 |
| WO | 2011/003551 A2 | 1/2011 |

OTHER PUBLICATIONS

Extended EP Search Report dated Oct. 4, 2017 corresponding to EP patent application No. 17181697.8.

* cited by examiner

*Primary Examiner* — Eisa B Elhilo

(74) *Attorney, Agent, or Firm* — Posz Law Group, PLC

(57) ABSTRACT

A first agent for oxidative hair dye of the present disclosure includes: an (A) component, which is at least one selected from the group consisting of resorcin, derivatives thereof, and salts thereof, in a content not exceeding 0.15% by mass; a (B) component, which is a coupler such as m-aminophenol, a (C) component, which is a dye intermediate such as p-phenylenediamine in a content between 0.01% by mass and 0.45% by mass; and a (D) component, which is an alkanolamine.

7 Claims, No Drawings

FIRST AGENT FOR OXIDATIVE HAIR DYE AND METHOD FOR STABILIZING COLOR TONE OF OXIDATIVE HAIR DYE COMPOSITION

BACKGROUND OF THE INVENTION

The present invention relates to a first agent for oxidative hair dye containing an alkanolamine, and a method for stabilizing the color tone of an oxidative hair dye composition.

There has been known a hair dye composition exhibiting effects by mixing a plurality of chemicals. As such a hair dye composition, for example, there has been known an oxidative hair dye composition composed of a first agent containing an alkaline agent and an oxidative dye, and a second agent containing an oxidant such as hydrogen peroxide. The oxidative dye can be selected as necessary from known dyes from the viewpoint of a desired color, a desired brightness, a desired saturation, and the like. For example, in the field of fashion colors generally demanding high brightness and high saturation, oxidative hair dye compositions containing a predetermined amount of m-aminophenol, 5-amino-o-cresol, α-naphthol, or the like as an oxidative dye are used.

The alkaline agent improves hair-dyeing power by facilitating the action of the oxidant contained in the second agent and by swelling hair and improving permeability of a dye into hair. Ammonia and the like have been conventionally known as an alkaline agent used for an oxidative hair dye composition. However, there has been a problem that ammonia is accompanied by irritant odor when the amount of ammonia compounded is increased.

For example, an oxidative hair dye composition disclosed in Japanese Patent Laid-Open No. 2004-26834 has been known. Japanese Patent Laid-Open No. 2004-26834 uses alkanolamine as an alkaline agent to achieve the reduction of the odor derived from ammonia and to improve the hair-dyeing power.

SUMMARY OF THE INVENTION

However, there is a problem that when an alkanolamine is compounded into an oxidative hair dye composition containing m-aminophenol or the like as an oxidative dye, such an alkanolamine sometimes degrades the stability of the dye.

Accordingly, an objective of the present invention is to provide an alkanolamine-containing first agent for oxidative hair dye capable of improving the stability of the dye, and a method for stabilizing the color tone of an oxidative hair dye composition.

The present invention is based on the finding that the use of resorcin or the like in an alkanolamine-containing first agent for oxidative hair dye improves the stability of the dye. It is to be noted that the numerical values representing the contents of the components in terms of percent by mass are the numerical values in a formulation including a solubilizer such as water.

To achieve the foregoing objective and in accordance with one aspect of the present invention, a first agent for oxidative hair dye is provided that includes: an (A) component, which is at least one selected from the group consisting of resorcin, derivatives thereof, and salts thereof, in a content not exceeding 0.15% by mass; a (B) component, which is at least one coupler selected from the group consisting of m-aminophenol, 5-amino-o-cresol, α-naphthol, 2,4-diaminophenoxyethanol, 5-(2-hydroxyethylamino)-2-methylphenol, derivatives thereof, and salts thereof; a (C) component, which is at least one dye intermediate selected from the group consisting of p-phenylenediamine, toluene-2,5-diamine, p-aminophenol, N,N-bis(2-hydroxyethyl)-p-phenylenediamine, derivatives thereof, and salts thereof, in a content between 0.01% by mass and 0.45% by mass; and a (D) component, which is an alkanolamine.

In the above described first agent for oxidative hair dye, the mass ratio of the content of the (B) component to the content of the (A) component in the first agent for oxidative hair dye may be 0.5 to 15. In the above described first agent for oxidative hair dye, the (B) component may comprise α-naphthol.

In accordance with another aspect of the present invention, a method for stabilizing a color tone of an oxidative hair dye composition including a first agent for oxidative hair dye is provided. The method includes forming the first agent for oxidative hair dye by mixing an (A) component, which at least one selected from the group consisting of resorcin, derivatives thereof, and salts thereof, a (B) component, which is at least one coupler selected from the group consisting of m-aminophenol, 5-amino-o-cresol, α-naphthol, 2,4-diaminophenoxyethanol, 5-(2-hydroxyethylamino)-2-methylphenol, derivatives thereof, and salts thereof, a (C) component, which at least one dye intermediate selected from the group consisting of p-phenylenediamine, toluene-2,5-diamine, p-aminophenol, N,N-bis(2-hydroxyethyl)-p-phenylenediamine, derivatives thereof, and salts thereof, and a (D) component, which is an alkanolamine. The content of the (A) component is 0.15% by mass or less and the content of the (C) component is 0.01 to 0.45% by mass of the first agent for oxidative hair dye.

Other aspects and advantages of the present invention will become apparent from the following detailed description illustrating by way of example the principles of the present invention.

DETAILED DESCRIPTION OF THE PREFERRED EMBODIMENTS

Hereinafter, a first agent for oxidative hair dye according to one embodiment of the present invention will be described. The first agent for oxidative hair dye (hereinafter, simply referred to as "the first agent") of the present embodiment is constituted as the first agent of a two-part type oxidative hair dye composition. The two-part type oxidative hair dye composition is composed of, for example, a first agent containing at least an alkanolamine and a predetermined oxidative dye, and a second agent containing at least an oxidant. In the oxidative hair dye composition, after a mixture is prepared by mixing the first agent and the second agent, the mixture is used for a hair dyeing treatment.

<First Agent>

The first agent contains, in addition to the alkaline agent and the dye, an (A) component selected from at least one of resorcin, derivatives thereof, and salts thereof to improve the stability of the oxidative dye.

The alkanolamine as a (D) component is compounded as an alkaline agent, and improves the brightness of hair. Specific examples of the alkanolamine include monoethanolamine, diethanolamine, triethanolamine, monoisopropanolamine, diisopropanolamine, and triisopropanolamine.

The lower limit of the content of the alkanolamine of the (D) component in the first agent is appropriately set, and is preferably 1.5% by mass or more, and more preferably 3% by mass or more. When the content of the alkanolamine of the (D) component is 1.5% by mass or more, the stability of the oxidative dye tends to be degraded by the alkanolamine, and accordingly the effect of the (A) component on improving the stability of the oxidative dye is more expected. In addition, when ammonia is used in combination as an alkaline agent, the mixing amount of ammonia can be reduced, and accordingly the reduction effect on the irritant odor from ammonia can also be expected.

The upper limit of the content of the alkanolamine of the (D) component in the first agent is appropriately set, and is preferably 20% by mass or less, more preferably 15% by mass or less, and furthermore preferably 10% by mass or less. When the content of the alkanolamine of the (D) component is 20% by mass or less, the damage of hair is more suppressed.

As the alkaline agent, the alkanolamines listed above may be used alone, together, or in combination with an alkaline agent(s) other than the alkanolamine. Examples of the alkaline agent other than the alkanolamine include ammonia, a carbonate, a silicate, a metasilicate, a sulfate, a chloride, a phosphate, an organic amine, a basic amino acid, and the hydroxide of an alkali metal or an alkaline earth metal. Specific examples of the carbonate include sodium carbonate, sodium hydrogen carbonate, potassium carbonate, potassium hydrogen carbonate, lithium carbonate, calcium carbonate, magnesium carbonate, barium carbonate, guanidine carbonate, guanidine hydrogen carbonate, ammonium carbonate, and ammonium hydrogen carbonate. Specific examples of the silicate include sodium silicate and potassium silicate. Specific examples of the metasilicate include sodium metasilicate and potassium metasilicate. Specific examples of the sulfate include ammonium sulfate. Specific examples of the chloride include ammonium chloride. Specific examples of the phosphate include monoammonium phosphate and diammonium phosphate. Specific examples of the organic amine include 2-amino-2-methyl-1-propanol (AMP), 2-amino-2-methyl-1,3-propanediol, and guanidine. Specific examples of the basic amino acid include arginine and lysine. Specific examples of the hydroxide of the alkali metal or the alkaline earth metal include sodium hydroxide and potassium hydroxide. These alkaline agents other than the alkanolamine may be contained alone or in combination of two or more. Among these, from the viewpoint of the improvement of the hair-dyeing power, ammonia and ammonium salts are preferably used.

When an alkaline agent other than the alkanolamine is used in combination, the mass ratio of the content of the alkanolamine to the content of the whole alkaline agents in the mixture of the first agent and the second agent is not particularly limited, but is preferably 0.2 or more, and more preferably 0.3 or more, from the viewpoint of exhibiting the irritant odor reduction effect of the alkanolamine. In other words, the proportion of the content of the alkaline agent other than the alkanolamine in the whole alkaline agents is preferably 80% by mass or less, and more preferably 70% by mass or less. The lower limit of the proportion of the content of the alkaline agent other than the alkanolamine in the whole alkaline agents is not particularly limited, but is preferably 0.1% by mass or more, and more preferably 0.3% by mass or more, from the viewpoint of the improvement of the brightness.

The alkaline agent is preferably compounded in such an amount that the pH of the mixture of the first agent and the second agent, namely, the oxidative hair dye composition at the time of use is 7 to 12. When the pH of the mixture is adjusted to be 7 or more, the action of the oxidant contained in the second agent is more promoted. When the pH of the mixture is adjusted to be 12 or less, the damage of hair is more suppressed. It is to be noted that the pH of the oxidative hair dye composition is measured at 25° C. using the oxidative hair dye composition dissolved in water at a concentration of 10% by mass.

The oxidative dye is a compound capable of developing a color due to the oxidation polymerization caused by the oxidant contained in the second agent, and is classified into a dye intermediate and a coupler, and an oxidative dye includes a dye intermediate and a coupler. A coupler develops a color by bonding to a dye intermediate. In the present application, the (A) component is not included in the coupler as the oxidative dye.

Examples of the dye intermediate used in the present embodiment include the (C) component: at least one selected from p-phenylenediamine, toluene-2,5-diamine, p-aminophenol, N,N-bis(2-hydroxyethyl)-p-phenylenediamine, derivatives thereof, and salts thereof. Specific examples of the salts include hydrochlorides and sulfates. These specific examples of the dye intermediate may be contained alone or in combination of two or more. The (C) component as the dye intermediate allows high brightness and high saturation to be obtained by being used in combination with the coupler as the below-described (B) component. In particular, in the field of fashion colors demanding high brightness and high saturation, the (C) component as the dye intermediate provides a favorable color tone.

The lower limit of the content of the (C) component in the first agent is 0.01% by mass or more, preferably 0.02% by mass or more, and more preferably 0.05% by mass or more. When the content of the dye intermediate of the (C) component is 0.01% by mass or more, the saturation among other things is more improved.

The upper limit of the content of the (C) component in the first agent is 0.45% by mass or less, preferably 0.4% by mass or less, and more preferably 0.3% by mass or less. When the content of the dye intermediate of the (C) component is 0.45% by mass or less, the brightness and the saturation is more improved.

As the dye intermediate, a component(s) other than the above-described (C) component may be used in combination within a range not impairing the advantageous effects of the present invention. Examples of such a dye intermediate include N-phenyl-p-phenylenediamine, 4,4'-diaminodiphenylamine, o-aminophenol, p-methylaminophenol, 2-hydroxyethyl-p-phenylenediamine, o-chloro-p-phenylenediamine, 4-amino-m-cresol, 2-amino-4-hydroxyethylaminoanisole, 2,4-diaminophenol, 1-hydroxyethyl-4,5-diaminopyrazole, derivatives thereof, and salts thereof. Specific examples of the salts include hydrochlorides and sulfates. These specific examples of the dye intermediate may be contained alone or in combination of two or more.

The mass ratio of the content of the (C) component to the content of the whole dye intermediates in the first agent is not particularly limited, but is preferably 0.3 or more, more preferably 0.5 or more, and furthermore preferably 0.7 or more, from the viewpoint of obtaining the color tone derived from the (C) component.

Examples of the coupler used in the present embodiment include the (B) component: at least one selected from m-aminophenol, 5-amino-o-cresol, α-naphthol, 2,4-diaminophenoxyethanol, 5-(2-hydroxyethylamino)-2-methylphenol, derivatives thereof, and salts thereof. Specific examples of the salts include hydrochlorides and sulfates. Moreover, examples of a salt of 2,4-diaminophenoxyethanol include 2,4-diaminophenoxyethanol hydrochloride. These specific examples of the coupler may be contained alone or in combination of two or more. Among these (B) components, α-naphthol is preferably contained from the viewpoint of being excellent in fading inhibition. Two or more (B) components are preferably contained from the viewpoint of being easily capable of achieving color tone variation. When used in combination with the (C) component, the (B) component allows high brightness and high saturation to be obtained. In particular, in the field of fashion colors demanding high brightness and high saturation, a favorable color tone is achieved.

The lower limit of the content of the (B) component in the first agent is appropriately set, and is preferably 0.005% by mass or more, more preferably 0.01% by mass or more, and furthermore preferably 0.05% by mass or more. When the content of the (B) component is 0.005% by mass or more, the saturation among other things is more improved.

The upper limit of the content of the (B) component in the first agent is appropriately set, and is preferably 1.5% by mass or less, more preferably 1% by mass or less, and furthermore preferably 0.5% by mass or less. When the content of the (B) component is 1.5% by mass or less, the brightness among other things is more improved.

As a coupler, a component(s) other than the (B) component may be used in combination within the range not impairing the advantageous effects of the present invention. Examples of such a coupler include m-phenylenediamine, toluene-3,4-diamine, 2,6-diaminopyridine, diphenylamine, N,N-diethyl-m-aminophenol, phenylmethylpyrazolone, 1,5-dihydroxynaphthalene, derivatives thereof, and salts thereof. Specific examples of the salts include hydrochlorides and sulfates. These specific examples of the coupler may be contained alone or in combination of two or more.

The mass ratio of the content of the (B) component to the content of the whole couplers in the first agent is not particularly limited, but is preferably 0.5 or more, more preferably 0.6 or more, and furthermore preferably 0.7 or more, from the viewpoint of obtaining the color tone derived from the (B) component.

Optionally, the first agent may contain an oxidative dye other than the above-described ones, for example, an oxidative dye listed in "The Japanese Standards of Quasi-Drug Ingredients" (published by Yakuji Nippo Ltd., June 2006).

The lower limit of the content of the whole oxidative dye(s) in the first agent is appropriately set, and is preferably 0.01% by mass or more, more preferably 0.05% by mass or more, and furthermore preferably 0.08% by mass or more. When the content of the whole oxidative dye(s) is 0.01% by mass or more, the saturation among other things is more improved.

The upper limit of the content of the whole oxidative dye(s) in the first agent is appropriately set, and is preferably 10% by mass or less, more preferably 7% by mass or less, and furthermore preferably 5% by mass or less. When the content of the whole oxidative dye(s) is 10% by mass or less, in particular in the case where a solubilizer is used, the solubility to the solubilizer is improved, and additionally the brightness is more improved.

The first agent contains the (A) component selected from at least one of resorcin, derivatives thereof, and salts thereof. Examples of the derivative of resorcin include an alkylated resorcin and a halogenated resorcin. Specific examples of the alkylated resorcin include 2-methylresorcin. Specific examples of the halogenated resorcin include 4-chlororesorcin and 2-chlororesorcin. These resorcins may be contained alone or in combination of two or more. The (A) component improves the stability of the above-described oxidative dye, in particular the (B) component in the alkanolamine-containing first agent.

The lower limit of the content of the (A) component in the first agent is appropriately set, and is preferably 0.005% by mass or more, more preferably 0.01% by mass or more, and furthermore preferably 0.03% by mass or more. When the content of the (A) component is 0.005% by mass or more, the stability of the oxidative dye is more improved.

The upper limit of the content of the (A) component in the first agent is 0.15% by mass or less, preferably 0.1% by mass or less, and more preferably 0.08% by mass or less. When the content of the (A) component is 0.15% by mass or less, the development of the color tone derived from the (A) component is suppressed, and the saturation is more improved.

The lower limit of the mass ratio of the content of the (B) component to the content of the (A) component in the first agent is preferably 0.5 or more, more preferably 0.6 or more, and furthermore preferably 0.7 or more. When the mass ratio is 0.5 or more, the saturation among other things is more improved.

The upper limit of the mass ratio of the content of the (B) component to the content of the (A) component in the first agent is preferably 15 or less, more preferably 10 or less, and furthermore preferably 9 or less. When the mass ratio is 15 or less, the stability of the color tone among other things is more improved.

The first agent may further contain, if necessary, a component other than the above-described components, such as a solubilizer, a water-soluble polymer, an oily component, a polyhydric alcohol, a surfactant, a sugar, a preservative, a stabilizer, a pH adjuster other than the above-described pH adjusters, a plant extract, a crude drug extract, a vitamin, a perfume, an antioxidant, an ultraviolet absorber, a chelating agent, and an oxidizing aid.

The solubilizer is compounded, for example, in the case where the first agent is made in a liquid form. Examples of the solubilizer used include a solvent such as water and an organic solvent. Specific examples of the organic solvent include ethanol, n-propanol, isopropanol, methyl cellosolve, ethyl cellosolve, methyl carbitol, ethyl carbitol, benzyl alcohol, phenethyl alcohol, γ-phenylpropyl alcohol, cinnamic alcohol, anise alcohol, p-methylbenzyl alcohol, α-dimethylphenethyl alcohol, α-phenylethanol, ethylene glycol phenyl ether (phenoxyethanol), phenoxyisopropanol, 2-benzyloxyethanol, an N-alkylpyrrolidone, an alkylene carbonate, and an alkyl ether. These solubilizers may be contained alone or in combination of two or more. Among these, water is excellent in the capability of dissolving the other components in the first agent and therefore is preferably used. When water is used as the solvent, the content of water in the mixture of the first agent and the second agent (the content at the time of use) is preferably 50% by mass or more and more preferably 60% by mass or more.

A water-soluble polymer imparts an adequate viscosity to the oxidative hair dye composition. Accordingly, the first agent may contain a water-soluble polymer within a range not impairing the advantageous effects of the present invention. Examples of the water-soluble polymer include a natural polymer, a semisynthetic polymer, a synthetic polymer, and an inorganic polymer. Specific examples of the natural polymer include guar gum, locust bean gum, quince seed, carrageenan, galactan, gum arabic, tragacanth gum, pectin, mannan, xanthan gum, dextran, succinoglucan, curdlan, hyaluronic acid, gelatin, casein, albumin, collagen, dextrin, and triglucopolysaccharide (pullulan).

Specific examples of the semisynthetic polymer include methyl cellulose, ethyl cellulose, hydroxyethyl cellulose, hydroxyethyl cellulose dimethyl diallyl ammonium chloride, hydroxypropyl cellulose, carboxymethyl cellulose, sodium carboxymethyl cellulose, hydroxypropyl methyl cellulose, cationized cellulose, cationized guar gum, starch phosphate, propylene glycol alginate, and an alginate.

Specific examples of the synthetic polymer include polyvinyl caprolactam, polyvinyl alcohol (PVA), polyvinylpyrrolidone (PVP), vinylpyrrolidone-vinyl acetate (VP/VA) copolymer, polyvinyl butylal, polyvinyl methyl ether, carboxyvinyl polymer, sodium polyacrylate, polyacrylamide, polyethylene oxide, ethylene oxide-propylene oxide block copolymer, acrylic acid/alkyl acrylate copolymer, polydimethylmethylene piperidinium chloride (polyquaternium-6) (Merquat 100: manufactured by Merck & Co., Inc.), and a copolymer composed of a semi-ester of itaconic acid and polyoxyethylene (hereinafter, referred to as "POE") alkyl ether, or an ester of methacrylic acid and a POE alkyl ether, and at least one monomer selected from acrylic acid, methacrylic acid and alkyl esters of these acid. These water-soluble polymers may be contained alone or in combination of two or more.

The oily component gives hair moist feeling. Accordingly, the first agent may contain an oily component within a range not impairing the advantageous effects of the present invention. Examples of the oily component include an oil/fat, a wax, a higher alcohol, a hydrocarbon, a higher fatty acid, an alkyl glyceryl ether, an ester, and a silicone.

Specific examples of the oil/fat include *Argania spinosa* kernel oil, lanolin, olive oil (purified olive oil), *camellia* oil, shea fat, almond oil, safflower oil, sunflower oil, soybean oil, cottonseed oil, sesame oil, corn oil, rapeseed oil, rice bran oil, rice germ oil, grape seed oil, avocado oil, macadamia nut oil, castor oil, coconut oil, and evening primrose oil. Specific examples of the wax include beeswax, candelilla wax, carnauba wax, jojoba oil, and lanolin wax. Specific examples of the higher alcohol include cetyl alcohol (cetanol), 2-hexyldecanol, stearyl alcohol, isostearyl alcohol, cetostearyl alcohol, oleyl alcohol, arachidyl alcohol, behenyl alcohol, 2-octyldodecanol, lauryl alcohol, myristyl alcohol, decyltetradecanol, and lanolin alcohol.

Specific examples of the hydrocarbon include paraffin, olefin oligomer, polyisobutene, hydrogenated polyisobutene, mineral oil, squalane, polybutene, polyethylene, microcrystalline wax, and vaseline. Specific examples of the higher fatty acid include lauric acid, myristic acid, palmitic acid, stearic acid, behenic acid, isostearic acid, 12-hydroxystearic acid, oleic acid, and lanolin fatty acid. Specific examples of the alkyl glyceryl ether include batyl alcohol, chimyl alcohol, selachyl alcohol, and isostearyl glyceryl ether.

Specific examples of the ester include diisopropyl adipate, isopropyl myristate, cetyl octanoate, isononyl isononanoate, octyldodecyl myristate, isopropyl palmitate, stearyl stearate, myristyl myristate, isotridecyl myristate, 2-ethylhexyl palmitate, octyldodecyl ricinoleate, a fatty acid cholesteryl/lanosteryl having 10 to 30 carbon atoms, cetyl lactate, lanolin acetate, ethylene glycol di-2-ethylhexanoate, pentaerythritol fatty acid ester, dipentaerythritol fatty acid ester, cetyl caprate, glyceryl tricaprylate, diisostearyl malate, dioctyl succinate, and cetyl 2-ethylhexanoate.

Specific examples of the silicone include dimethylpolysiloxane (dimethicone), methylphenylpolysiloxane, decamethylcyclopentasiloxane, dodecamethylcyclohexasiloxane, a terminal hydroxyl group-modified dimethylpolysiloxane, a high polymerization silicone, a polyether-modified silicone (for example, (PEG/PPG/butylene/dimethicone) copolymer), an amino-modified silicone, a betaine-modified silicone, an alkyl-modified silicone, an alkoxy-modified silicone, a mercapto-modified silicone, a carboxy-modified silicone, and a fluorine-modified silicone. These oily components may be contained alone or in combination of two or more.

Examples of the polyhydric alcohol include a glycol and glycerin. Specific examples of the glycol include ethylene glycol, diethylene glycol, triethylene glycol, polyethylene glycol, high-polymerization polyethylene glycol, propylene glycol, dipropylene glycol, polypropylene glycol, isoprene glycol, and 1,3-butylene glycol. Specific examples of the glycerin include glycerin, diglycerin, and polyglycerin. These polyhydric alcohols may be contained alone or in combination of two or more.

The surfactant emulsifies or solubilizes the oxidative hair dye composition at the time of use as an emulsifier or as a component that solubilizes respective components to adjust viscosity or improve the stability of viscosity. Accordingly, the first agent may contain a surfactant within a range not impairing the advantageous effects of the present invention. Examples of the surfactant include an anionic surfactant, a cationic surfactant, an amphoteric surfactant, and a nonionic surfactant.

Specific examples of the anionic surfactant include an alkyl ether sulfate, an alkyl sulfate, an alkyl ether sulfate ester salt, an alkenyl ether sulfate, an alkenyl sulfate, an olefin sulfonate, an alkane sulfonate, a saturated or unsaturated fatty acid salt, an alkyl or alkenyl ether carboxylate, an α-sulfofatty acid salt, an N-acylamino acid-type surfactant, a phosphate mono- or di-ester-type surfactant, a sulfosuccinic acid ester, an N-alkyloylmethyl taurine salt, and derivatives thereof. Specific examples of the counterion of the anionic group of these surfactants include sodium ion, potassium ion, and triethanolamine. More specifically, examples of the alkyl ether sulfate include sodium POE lauryl ether sulfate. Specific examples of the alkyl sulfate include sodium lauryl sulfate and sodium cetyl sulfate. Specific examples of the derivative of the alkyl sulfate include sodium POE lauryl sulfate. Specific examples of the phosphoric acid ester-type surfactant include POE oleyl ether phosphate.

Specific examples of the cationic surfactant include lauryl trimethyl ammonium chloride, cetyl trimethyl ammonium chloride, stearyl trimethyl ammonium chloride, alkyl trimethyl ammonium chloride, distearyl dimethyl ammonium chloride, cetyl trimethyl ammonium bromide, stearyl trimethyl ammonium bromide, lanolin fatty acid aminopropyl ethyl dimethyl ammonium ethyl sulfate, stearyl trimethyl ammonium saccharin, cetyl trimethyl ammonium saccharin, methacryloyloxy ethyl trimethyl ammonium chloride, behenyl trimethyl ammonium methyl sulfate, behenyl dimethyl amine, behenic acid diethyl aminoethyl amide, behenic acid dimethyl aminopropyl amide, behenic acid dimethyl aminoethyl amide, stearyl dimethyl amine, palmitoxypropyl dimethylamine, stearoxypropyl dimethylamine, and stearic acid dimethyl aminopropyl amide. Specific examples of the alkyl trimethyl ammonium chloride include behenyl trimethyl ammonium chloride and arachidyl trimethyl ammonium chloride.

Specific examples of the amphoteric surfactant include coco-betaine, lauramidopropyl betaine, cocamidopropyl betaine, sodium lauroamphoacetate, sodium cocoamphoacetate, coconut oil fatty acid amidopropyl betaine, lauryl betaine (betaine lauryldimethylamino acetate), and sodium laurylaminopropionate.

Specific examples of the nonionic surfactant include an ether-type nonionic surfactant, an ester-type nonionic surfactant, and an alkyl glucoside. Specific examples of the ether-type nonionic surfactant include POE cetyl ether (ceteth), POE stearyl ether (steareth), POE behenyl ether, POE oleyl ether (oleth), POE lauryl ether (laureth), POE octyl dodecyl ether, POE hexyl decyl ether, POE isostearyl ether, POE nonyl phenyl ether, POE octyl phenyl ether, POE polyoxypropylene cetyl ether, and POE polyoxypropylene decyl tetradecyl ether.

Specific examples of the ester-type nonionic surfactant include POE sorbitan monooleate, POE sorbitan monostearate, POE sorbitan monopalmitate, POE sorbitan monolaurate, POE sorbitan trioleate, POE glycerin monostearate, POE glycerin monomyristate, POE sorbit tetraoleate, POE sorbit hexastearate, POE sorbit monolaurate, POE sorbit bees wax, polyethylene glycol monooleate, polyethylene glycol monostearate, polyethylene glycol monolaurate, lipophilic glycerin monooleate, lipophilic glycerin monostearate, self-emulsifying glycerin monostearate, sorbitan monooleate, sorbitan sesquioleate, sorbitan trioleate, sorbitan monostearate, sorbitan monopalmitate, sorbitan monolaurate, a sucrose fatty acid ester, decaglyceryl monolaurate, decaglyceryl monostearate, decaglyceryl monooleate, and decaglyceryl monomyristate.

Specific examples of the alkyl glucoside include an alkyl (having 8 to 16 carbon atoms) glucoside, POE methyl glucoside, and POE methyl glucoside dioleate. These specific examples of the surfactant may be contained alone or in combination of two or more.

Example of the sugar include: monosaccharides such as glucose and galactose; disaccharides such as maltose, sucrose, fructose, and trehalose; and a sugar alcohol. Specific examples of the preservative include paraben, methylparaben, and sodium benzoate. Specific examples of the stabilizer include phenacetin, 8-hydroxyquinoline, acetanilide, sodium pyrophosphate, barbituric acid, uric acid, and tannic acid.

A pH adjuster may be compounded in order to adjust the pH of the oxidative hair dye composition. The pH adjuster is selected from the known pH adjusters. Examples of the pH adjuster include an inorganic acid, an organic acid, and a salt thereof. Specific examples of the organic acid include citric acid, glycolic acid, succinic acid, tartaric acid, lactic acid, malic acid, levulinic acid, acetic acid, butyric acid, valeric acid, oxalic acid, maleic acid, fumaric acid, and mandelic acid. Specific examples of the organic acid salt include a sodium salt and a potassium salt. Specific examples of the inorganic acid include phosphoric acids such as phosphoric acid and pyrophosphoric acid, hydrochloric acid, sulfuric acid, and nitric acid. These may be used alone or in combination of two or more.

Examples of the antioxidant include an ascorbic acid and a sulfite. Examples of the chelating agent include edetic acid (ethylenediaminetetraacetic acid (EDTA)), disodium edetate, tetrasodium edetate, diethylenetriaminepentaacetic acid and salts thereof, ethylenediaminehydroxyethyl triacetic acid and salts thereof, and hydroxyethane diphosphonic acid (HEDP) and salts thereof.

The formulation of the first agent is not particularly limited; specific examples of the formulation include the formulations that are in a liquid state at 25° C. such as an aqueous solution or an emulsion; and the formulations that are in a gel state, a foam state, a cream state, and a solid state at 25° C. Among these, a cream formulation is preferable from the viewpoint of being excellent in the storage stability of the dye. Alternatively, the formulation of the first agent can be, for example, an aerosol or a nonaerosol. When the formulation of the first agent is a nonaerosol, the formulation can further take various forms such as a squeeze foamer type formulation and a pump foamer type formulation. In the case of an aerosol, a known propellant and a known foaming agent can be applied. Specific examples of the propellant and foaming agent include liquefied petroleum gas (LPG), dimethyl ether (DME), nitrogen gas and carbon dioxide gas.

<Second Agent>

The second agent can contain the foregoing solubilizer in addition to the oxidant. The oxidant further improves decolorization property for melanin contained in hair. Specific examples of the oxidant include hydrogen peroxide, urea peroxide, melamine peroxide, sodium percarbonate, potassium percarbonate, sodium perborate, potassium perborate, ammonium persulfate, potassium persulfate, sodium persulfate, sodium peroxide, potassium peroxide, magnesium peroxide, barium peroxide, calcium peroxide, strontium peroxide, hydrogen peroxide adducts of sulfates, hydrogen peroxide adducts of phosphates, and hydrogen peroxide adducts of pyrophosphates. These specific examples of the oxidant may be contained alone or in combination of two or more. The content of the oxidant in the second agent is appropriately set, and is preferably 1.0% by mass or more, more preferably 2.0% by mass or more, and furthermore preferably 3.0% by mass or more. When the content of the oxidant is 1.0% by mass or more, the decolorization property for melamine is more improved. The content of the oxidant in the second agent is preferably 15.0% by mass or less, more preferably 9.0% by mass or less, and furthermore preferably 6.0% by mass or less. When the content of the oxidant is 15.0% by mass or less, the damage of hair, or the like is more suppressed.

When hydrogen peroxide is compounded as an oxidant in the second agent, the second agent preferably contains a stabilizer such as sodium stannate, ethylene glycol phenyl ether (phenoxyethanol), hydroxyethane diphosphonic acid or a salt thereof to improve the stability of hydrogen peroxide. Examples of the hydroxyethane diphosphonic acid salt include tetrasodium hydroxyethane diphosphonate and disodium hydroxyethane diphosphonate. The second agent may contain the components that are generally contained in an oxidative hair dye composition and that do not inhibit the actions of the foregoing respective components. For example, the second agent may appropriately contain the foregoing components contained in the first agent within the range not impairing the advantageous effects of the present invention.

The formulation of the second agent is not particularly limited; specific examples of the formulation include the formulations that are in a liquid state at 25° C. such as an aqueous solution or an emulsion; and the formulations that are in a gel state, a foam state, a cream state, and a solid state at 25° C. Alternatively, the formulation of the second agent can be, for example, an aerosol or a nonaerosol. When the formulation of the second agent is a nonaerosol, the formulation can further take various forms such as a squeeze foamer type formulation and a pump foamer type formulation. In the case of an aerosol, a known propellant and a known foaming agent can be applied. When the oxidative hair dye composition is used, a mixture is prepared by mixing the first agent and the second agent with each other. Subsequently, a necessary amount of the mixture is attached to hands with thin gloves, a comb or a brush, and applied to hair.

Next, the operation of the first agent of the present embodiment will be described.

The stability of the oxidative dye is sometimes degraded depending on the type of the oxidative dye used, the combination with the alkaline agent, and the like. For example, when a carbonate is used as the alkaline agent and a specific oxidative dye such as m-aminophenol is used in a predetermined amount, the stability may be degraded. The applicant has already filed a patent application for an oxidative hair dye composition in which the degradation of the stability of the oxidative dye is suppressed by resorcin or the like (Japanese Patent Application No. 2015-010747). As a result of further research, the applicant has found that the tendency of the degradation of the stability varies depending on the type of the oxidative dye in the case where a carbonate is used as the alkaline agent and in the case where an alkanolamine is used as the alkaline agent. For example, in the case where 2,4-diaminophenoxyethanol is used as the oxidative dye, the stability of the oxidative dye tends to be degraded when combined with an alkanolamine as the alkaline agent. When the mixing amount of the oxidative dye is increased, the oxidative dye can be stabilized but the brightness can be degraded. Therefore, it is not easy to improve the stability of the oxidative dye while obtaining the desired brightness. In the present invention, by adding a specific amount of an aromatic compound such as resorcin as the (A) component, the storage stability of the oxidative dye such as 2,4-diaminophenoxyethanol is improved even in the case of a long-term storage, and accordingly the change of the color tone is suppressed. Additionally, it is not necessary to regulate the mixing amount of the oxidative dye for the purpose of improving the stability of the oxidative dye, and thus from such a viewpoint, the change of the color tone is suppressed.

The first agent according to the present embodiment has the following advantages.

(1) The present embodiment uses as the (A) component a predetermined amount of resorcin or the like in the alkanolamine-containing first agent. Accordingly, it is possible to improve the stability of the oxidative dye, more specifically the (B) component, namely at least one coupler selected from m-aminophenol, 5-amino-o-cresol, α-naphthol, 2,4-diaminophenoxyethanol, 5-(2-hydroxyethylamino)-2-methylphenol, derivatives thereof, and salts thereof. Consequently, even in the case of a long-term storage, the change of the color tone is suppressed.

(2) The present embodiment includes, as the oxidative dye, 0.01 to 0.45% by mass of the (C) component, namely at least one dye intermediate selected from p-phenylenediamine, toluene-2,5-diamine, p-aminophenol, N,N-bis(2-hydroxyethyl)-p-phenylenediamine, derivatives thereof, and salts thereof. Accordingly, the brightness and the saturation is more improved. Consequently, the first agent of the present embodiment is suitably used, in particular, in the field of fashion colors demanding high brightness and high saturation.

(3) In the present embodiment, when the mass ratio of the content of the (B) component to the content of the (A) component in the first agent is set to fall within a range from 0.5 to 15, the brightness and the saturation are more improved.

(4) In the present embodiment, when α-naphthol is contained as the (B) component, the fading of the dyed hair is further inhibited.

The above-described embodiment may be modified as follows.

In the above-described embodiment, a direct dye listed in, for example, "The Japanese Standards of Quasi-Drug Ingredients" (published by Yakuji Nippo Ltd., June 2006) may be optionally contained as a dye other than the foregoing oxidative dye within a range not impairing the advantageous effects of the present invention.

In the above-described embodiment, a multiple part-type oxidative hair dye composition is provided including the first agent containing the alkanolamine of the (D) component and the oxidative dye, and others, and the second agent containing the oxidant and others. However, the oxidative hair dye composition is not limited to the two-part type. That is, as long as the (A) to (D) components are mixed in the same agent, some of the components of the first agent and the second agent may constitute an additional agent to form a three or more part type composition.

In the above-described embodiment, the field to which the first agent is applied is not particularly limited. However, the first agent is preferably applied to the field of fashion colors, which demand high brightness and high saturation.

The above-described embodiment may be constituted as a method for stabilizing the color tone of the oxidative hair dye composition including the first agent for oxidative hair dye, which contains the (A) to (D) components.

EXAMPLES

Next, the foregoing embodiments will be described more specifically with reference to Examples and Comparative Examples. It is to be noted that the present invention is not limited to the constitutions described in the Examples section.

Formulation Example 1

In each of Examples and Comparative Examples, a first agent and a second agent of a cream oxidative hair dye composition that contained the respective components shown in Tables 1 to 3 were prepared. The numerical values in the row of each of the components shown in Tables 1 to 3 represent the contents of the component concerned, expressed in percent by mass (this is also the case in Table 4 and the subsequent tables). In each of Examples and Comparative Examples, the first agent and the second agent were mixed in a mass ratio of 1:1 to prepare an oxidative hair dye composition. The obtained oxidative hair dye composition was applied with a brush to a tuft of black hair and a tuft of white hair (10 cm, manufactured by Beaulax Co., Ltd.) (hereinafter, simply referred to as hair tuft), and the hair tufts were allowed to stand at room temperature (25° C.) for 30 minutes. Next, the oxidative hair dye composition attached to the hair tufts was washed away with water, then the hair tufts were shampooed twice (by using Bigen treatment shampoo manufactured by Hoyu Co., Ltd.) and conditioned once (by using Bigen treatment conditioner manufactured by Hoyu Co., Ltd.). Subsequently, the hair tufts were blow-dried with warm air, and then allowed to stand for a day. For the hair tufts subjected to the hair dyeing treatment was evaluated for the brightness and the saturation according to the following methods. The hair dyeing treatment was also performed using the first agent of each of Examples and Comparative Examples that was stored for a predetermined period of time, and the change of the color tone of the hair tufts was evaluated according to the following method. The symbols "(A)" to "(D)" in the tables represent the compounds corresponding to the (A) to (D) components described in the claims of the present application. The symbol "b" in the tables represents a compound for comparison with the (B) component described in the claims of the present application.

<Brightness>

Ten panelists visually observed, under a standard light source, the brightness of the human hair tufts after being treated with each of the oxidative hair dye compositions, and scored by four-grade evaluation of 4 points, 3 points, 2 points and 1 point. The scoring results of the panelists were averaged; the brightness was rated as "Very good" for the average score of 3.6 or more, as "Good" for the average score of 2.6 or more and less than 3.6, as "Not good" for the average score of 1.6 or more and less than 2.6, and as "Poor" for the average score of less than 1.6; thus, the evaluation results were obtained. The results thus obtained are shown in Tables 1 and 2.

<Saturation>

Ten panelists visually observed, under a standard light source, the saturation of the human hair tufts after being treated with each of the oxidative hair dye compositions, and scored by four-grade evaluation of 4 points, 3 points, 2 points and 1 point. The scoring results of the panelists were averaged; the saturation was rated as "Very good" for the average score of 3.6 or more, as "Good" for the average score of 2.6 or more and less than 3.6, as "Not good" for the average score of 1.6 or more and less than 2.6, and as "Poor" for the average score of less than 1.6; thus, the evaluation results were obtained. The results thus obtained are shown in Tables 1 and 2.

<Change of Color Tone>

The first agent of each of Examples and Comparative Examples was stored in a thermostatic chamber at 45° C. for 1 month. By using the first agent of each of Examples and Comparative Examples that had been stored for the predetermined period of time, the same hair dyeing treatment as described above was performed, and thus the treated hair tufts were obtained. The first agent of each of Examples and Comparative Examples that was not subjected to storing treatment was also used in the same hair dyeing treatment as described above, and thus the respective control hair tufts were prepared. Ten panelists visually observed each of the obtained hair tufts under a standard light source with respect to the presence or absence of change of the color tone (brightness and saturation) due to the application or non-application of the storing treatment, and evaluated the change of the color tone according to the following standards.

The obtained hair tufts were scored according to the following four-grade evaluation: the case where almost no change of the hair dyeing result was found as compared with the control was scored as 4 points; the case where a slight change of the hair dyeing result was found as compared with the control was scored as 3 points; the case where a slightly larger change of the hair dyeing result was found as compared with the control was scored as 2 points; and the case where a larger change of the hair dyeing result was found as compared with the control was scored as 1 point. The scoring results of the panelists were averaged and rated as "Very good" for the average score of 3.6 or more, as "Good" for the average score of 2.6 or more and less than 3.6, as "Not good" for the average score of 1.6 or more and less than 2.6, and as "Poor" for the average score of less than 1.6; thus, the evaluation results were obtained. The results thus obtained are shown in Tables 1 and 2.

TABLE 1

| | <First agent> | Example 1 | Example 2 | Example 3 | Example 4 | Example 5 | Comp. Example 1 |
|---|---|---|---|---|---|---|---|
| (A) | Resorcin | 0.05 | 0.05 | 0.05 | 0.05 | 0.05 | — |
| (C) | Toluene-2,5-diamine | 0.1 | 0.1 | 0.1 | 0.1 | 0.1 | 0.1 |
| (B) | α-Naphthol | 0.1 | — | — | — | — | 0.1 |
| | m-Aminophenol | — | 0.1 | — | — | — | — |
| | 5-Amino-o-cresol | — | — | 0.1 | — | — | — |
| | 2,4-Diaminophenoxyethanol hydrochloride | — | — | — | 0.1 | — | — |
| | 5-(2-hydroxymethylamino)-2-methylphenol | — | — | — | — | 0.1 | — |
| (b) | 4-Nitro-o-phenylenediamine | — | — | — | — | — | — |
| | POE(30) cetyl ether | 2 | 2 | 2 | 2 | 2 | 2 |
| | POE(2) cetyl ether | 1 | 1 | 1 | 1 | 1 | 1 |
| | Stearyl trimethyl ammonium chloride | 0.25 | 0.25 | 0.25 | 0.25 | 0.25 | 0.25 |
| | Vaseline | 3 | 3 | 3 | 3 | 3 | 3 |
| | Cetanol | 4 | 4 | 4 | 4 | 4 | 4 |
| | Stearyl alcohol | 3 | 3 | 3 | 3 | 3 | 3 |
| | L-Ascorbic acid | 0.5 | 0.5 | 0.5 | 0.5 | 0.5 | 0.5 |
| | 28% by mass Ammonia water | 4 | 4 | 4 | 4 | 4 | 4 |
| (D) | 70% by mass Monoethanolamine | 10 | 10 | 10 | 10 | 10 | 10 |
| | Ammonium chloride | 1.5 | 1.5 | 1.5 | 1.5 | 1.5 | 1.5 |
| | Purified water | Balance | Balance | Balance | Balance | Balance | Balance |
| | Total | 100 | 100 | 100 | 100 | 100 | 100 |
| | Mixing amount (% by mass) of (B) component in first agent | 0.1 | 0.1 | 0.1 | 0.1 | 0.1 | 0.1 |
| | Mixing amount (% by mass) of (C) component in first agent | 0.1 | 0.1 | 0.1 | 0.1 | 0.1 | 0.1 |

TABLE 1-continued

|  |  |  |  |  |  |  |  |
|---|---|---|---|---|---|---|---|
|  | Mixing amount (% by mass) of (D) component in first agent | 7 | 7 | 7 | 7 | 7 | 7 |
|  | Mass ratio (B)/(A) | 2 | 2 | 2 | 2 | 2 | — |
| Evaluation | Brightness | Very good | Very good | Very good | Good | Very good | Very good |
|  | Saturation | Very good | Very good | Very good | Very good | Very good | Very good |
|  | Change of color tone | Very good | Very good | Very good | Very good | Good | Poor |

|  | <First agent> | Comp. Example 2 | Comp. Example 3 | Comp. Example 4 | Comp. Example 5 | Comp. Example 6 |
|---|---|---|---|---|---|---|
| (A) | Resorcin | — | — | — | — | 0.05 |
| (C) | Toluene-2,5-diamine | 0.1 | 0.1 | 0.1 | 0.1 | 0.1 |
| (B) | α-Naphthol | — | — | — | — | — |
|  | m-Aminophenol | 0.1 | — | — | — | — |
|  | 5-Amino-o-cresol | — | 0.1 | — | — | — |
|  | 2,4-Diaminophenoxyethanol hydrochloride | — | — | 0.1 | — | — |
|  | 5-(2-hydroxymethylamino)-2-methylphenol | — | — | — | 0.1 | — |
| (b) | 4-Nitro-o-phenylenediamine | — | — | — | — | 0.1 |
|  | POE(30) cetyl ether | 2 | 2 | 2 | 2 | 2 |
|  | POE(2) cetyl ether | 1 | 1 | 1 | 1 | 1 |
|  | Stearyl trimethyl ammonium chloride | 0.25 | 0.25 | 0.25 | 0.25 | 0.25 |
|  | Vaseline | 3 | 3 | 3 | 3 | 3 |
|  | Cetanol | 4 | 4 | 4 | 4 | 4 |
|  | Stearyl alcohol | 3 | 3 | 3 | 3 | 3 |
|  | L-Ascorbic acid | 0.5 | 0.5 | 0.5 | 0.5 | 0.5 |
|  | 28% by mass Ammonia water | 4 | 4 | 4 | 4 | 4 |
| (D) | 70% by mass Monoethanolamine | 10 | 10 | 10 | 10 | 10 |
|  | Ammonium chloride | 1.5 | 1.5 | 1.5 | 1.5 | 1.5 |
|  | Purified water | Balance | Balance | Balance | Balance | Balance |
|  | Total | 100 | 100 | 100 | 100 | 100 |
|  | Mixing amount (% by mass) of (B) component in first agent | 0.1 | 0.1 | 0.1 | 0.1 | 0 |
|  | Mixing amount (% by mass) of (C) component in first agent | 0.1 | 0.1 | 0.1 | 0.1 | 0.1 |
|  | Mixing amount (% by mass) of (D) component in first agent | 7 | 7 | 7 | 7 | 7 |
|  | Mass ratio (B)/(A) | — | — | — | — | — |
| Evaluation | Brightness | Very good | Very good | Good | Very good | Very good |
|  | Saturation | Very good | Very good | Very good | Very good | Very good |
|  | Change of color tone | Poor | Poor | Poor | Poor | Poor |

TABLE 2

|  | <First agent> | Example 6 | Example 7 | Example 8 | Comp. Example 7 | Comp. Example 8 | Example 9 | Comp. Example 9 | Comp. Example 10 |
|---|---|---|---|---|---|---|---|---|---|
| (A) | Resorcin | 0.15 | 0.03 | 0.03 | 0.4 | 0.4 | 0.05 | 0.05 | 0.05 |
| (C) | Toluene-2,5-diamine | — | — | — | — | — | — | — | 0.1 |
|  | p-Phenylenediamine | 0.05 | 0.05 | 0.05 | 0.05 | 0.05 | 0.15 | 0.35 | — |
|  | p-Aminophenol | 0.05 | 0.05 | 0.05 | 0.05 | 0.05 | 0.2 | 0.2 | — |
| (B) | α-Naphthol | 0.03 | 0.05 | 0.05 | 0.05 | 0.03 | 0.05 | 0.05 | 0.1 |
|  | 5-Amino-o-cresol | 0.05 | 0.1 | 0.25 | 0.1 | 0.05 | 0.1 | 0.1 | — |
|  | POE(30) cetyl ether | 2 | 2 | 2 | 2 | 2 | 2 | 2 | 2 |
|  | POE(2) cetyl ether | 1 | 1 | 1 | 1 | 1 | 1 | 1 | 1 |
|  | Stearyl trimethyl ammonium chloride | 0.25 | 0.25 | 0.25 | 0.25 | 0.25 | 0.25 | 0.25 | 0.25 |
|  | Vaseline | 3 | 3 | 3 | 3 | 3 | 3 | 3 | 3 |
|  | Cetanol | 4 | 4 | 4 | 4 | 4 | 4 | 4 | 4 |
|  | Stearyl alcohol | 3 | 3 | 3 | 3 | 3 | 3 | 3 | 3 |
|  | L-Ascorbic acid | 0.5 | 0.5 | 0.5 | 0.5 | 0.5 | 0.5 | 0.5 | 0.5 |
|  | 28% by mass Ammonia water | 4 | 4 | 4 | 4 | 4 | 4 | 4 | 4 |

TABLE 2-continued

| <First agent> | | Example 6 | Example 7 | Example 8 | Comp. Example 7 | Comp. Example 8 | Example 9 | Comp. Example 9 | Comp. Example 10 |
|---|---|---|---|---|---|---|---|---|---|
| (D) | 70% by mass Monoethanolamine | 10 | 10 | 10 | 10 | 10 | 10 | 10 | — |
| | Ammonium chloride | 1.5 | 1.5 | 1.5 | 1.5 | 1.5 | 1.5 | 1.5 | 1.5 |
| | Purified water | Balance | Balance | Balance | Balance | Balance | Balance | Balance | Balance |
| | Total | 100 | 100 | 100 | 100 | 100 | 100 | 100 | 100 |
| | Mixing amount (% by mass) of (B) component in first agent | 0.08 | 0.15 | 0.3 | 0.15 | 0.08 | 0.15 | 0.15 | 0.1 |
| | Mixing amount (% by mass) of (C) component in first agent | 0.1 | 0.1 | 0.1 | 0.1 | 0.1 | 0.35 | 0.55 | 0.1 |
| | Mixing amount (% by mass) of (D) component in first agent | 7 | 7 | 7 | 7 | 7 | 7 | 7 | — |
| | Mass ratio (B)/(A) | 0.53 | 5 | 10 | 0.38 | 0.2 | 3 | 3 | 2 |
| Evaluation | Brightness | Very good | Very good | Very good | Very good | Very good | Good | Poor | Poor |
| | Saturation | Good | Very good | Very good | Not good | Poor | Good | Poor | Very good |
| | Change of color tone | Very good | Very good | Very good | Very good | Very good | Very good | Very good | Very good |

TABLE 3

| <Second agent> | |
|---|---|
| 35% by mass Hydrogen peroxide | 15.0 |
| Hydroxyethane diphosphonic acid | 0.2 |
| Tetrasodium hydroxyethane diphosphonate | 0.3 |
| Phenoxyethanol | 0.2 |
| Microcrystalline wax | 3.0 |
| Cetanol | 4.0 |
| Stearyl alcohol | 1.0 |
| POE(30) cetyl ether | 1.0 |
| POE(2) cetyl ether | 0.5 |
| Stearyl trimethyl ammonium chloride | 1.0 |
| Vaseline | 2.0 |
| Purified water | Balance |
| Total | 100 |

As shown in Tables 1 and 2, in the oxidative hair dye compositions using the first agents according to Examples, the evaluations of the brightness, the saturation, and the change of the color tone were higher than in Comparative Examples.

As shown in Table 1, in Comparative Examples 1 to 5 not containing resorcin, the evaluation of the change of the color tone was lower than in Examples. It was observed that Comparative Example 6 using a nitro dye in place of the coupler of the (B) component was not able to obtain the stability improvement effect of resorcin. A tendency was observed that was different from Japanese Patent Application No. 2015-010747 in which a carbonate was used as an alkaline agent and the stability improvement effect of resorcin was evaluated.

As shown in Table 2, Comparative Examples 7 and 8, in each of which the mixing amount of resorcin in the first agent was larger than 0.15% by mass, were lower in the evaluation of the saturation than Examples. It was observed that Comparative Example 9, in which the content of the (C) component in the first agent was larger than 0.45% by mass, was lower in the evaluations of the brightness and the saturation than Examples. It was observed that Comparative Example 10, not containing an alkanolamine, was lower in the evaluation of the brightness than Examples.

Formulation Example 2

In Formulation Example 2, a first agent and a second agent of an oxidative hair dye composition were prepared to be discharged in a foam state from an aerosol can. The first agent and the second agent each contained the components shown in Table 4. Each of the first agent and the second agent shown in Example 10 of Table 4 was charged into an aerosol can, which was then discharged in a foam state on a brush when used. The first agent and the second agent were discharged in a mass ratio of 1:1. Next, these two agents were mixed with each other while being applied with the brush to the same hair tufts as used in Formulation Example 1. Subsequent steps of the hair dyeing treatment were the same as those in Formulation Example 1. According to the methods shown in Formulation Example 1, the brightness, the saturation, and the change of the color tone were evaluated. The results are shown in Table 4. A comparative example different from Formulation Example 2 only in that resorcin was not mixed was also conducted (data not shown).

TABLE 4

| <First agent> | | Example 10 |
|---|---|---|
| (A) | Resorcin | 0.05 |
| (C) | p-Phenylenediamine | 0.1 |
| (B) | m-Aminophenol | 0.1 |
| | 28% by mass Ammonia water | 4.0 |
| (D) | 70% by mass Monoethanolamine | 10.0 |
| | POE(10) lauryl ether | 1.5 |
| | POE(10) cetyl ether | 1.0 |
| | Alkyl(C8 to 16) glucoside | 0.5 |
| | Stearyl trimethyl ammonium chloride | 0.5 |
| | Glycerin | 2.0 |
| | Cetanol | 0.7 |
| | Behenyl alcohol | 0.3 |
| | Olive oil | 3.0 |
| | Polyoctanium-6 | 0.5 |
| | Sodium sulfite | 0.3 |
| | Sodium diethylenetriamine pentaacetate | 0.3 |
| | Ascorbic acid | 0.5 |
| | Purified water | Balance |
| | Total | 100.0 |
| | Ratio of undiluted solution of above-listed components:propellant (LPG) | 95:5 |

TABLE 4-continued

| | <Second agent> | |
|---|---|---|
| | Myristyl alcohol | 0.2 |
| | Cetanol | 1.0 |
| | POE(10) lauryl ether | 0.5 |
| | POE(30) cetyl ether | 0.5 |
| | Stearyl trimethyl ammonium chloride | 0.2 |
| | Hydroxyethane diphosphonic acid | 0.1 |
| | Tetrasodium hydroxyethane diphosphonate | 0.2 |
| | Phenoxyethanol | 0.1 |
| | Phosphoric acid | Amount to give pH3 |
| | 35% by mass Hydrogen peroxide | 15.0 |
| | Purified water | Balance |
| | Total | 100.0 |
| | Ratio of undiluted solution of above-listed components:propellant (LPG) | 95:5 |
| Eval-uations | Brightness | Very good |
| | Saturation | Very good |
| | Change of color tone | Very good |

As shown in Table 4, the present formulation also showed superior evaluation results in particular for the change of the color tone and the like as compared with the comparative example.

Formulation Example 3

In Formulation Example 3, a first agent and a second agent of an oxidative hair dye composition were prepared to be discharged in a cream state from an aerosol can. The first agent and the second agent each contained the components shown in Table 5. Each of the first agent and the second agent shown in Example 11 of Table 5 was charged into an aerosol can, which was then discharged in a cream state on a brush when used. The first agent and the second agent were discharged in a mass ratio of 1:1. Next, these two agents were mixed with each other while being applied with the brush to the same hair tuft as used in Formulation Example 1. Subsequent steps of the hair dyeing treatment were the same as those in Formulation Example 1. According to the methods shown in Formulation Example 1, the brightness, the saturation, and the change of the color tone were evaluated. The results are shown in Table 5. A comparative example different from Formulation Example 3 only in that resorcin was not mixed was also conducted (data not shown).

TABLE 5

| | <First agent> | Example 11 |
|---|---|---|
| (A) | Resorcin | 0.05 |
| (C) | p-Phenylenediamine | 0.1 |
| (B) | m-Aminophenol | 0.1 |
| | 28% by mass Ammonia water | 4.0 |
| (D) | 70% by mass Monoethanolamine | 10.0 |
| | POE(30) cetyl ether | 2.0 |
| | POE(2) cetyl ether | 1.0 |
| | Stearyl trimethyl ammonium chloride | 0.25 |
| | Vaseline | 3.0 |
| | Cetanol | 4.0 |
| | Stearyl alcohol | 3.0 |
| | Ascorbic acid | 0.5 |
| | Purified water | Balance |
| | Total | 100.0 |
| | Ratio of undiluted solution:propellant (nitrogen gas) | 95:5 |

TABLE 5-continued

| | <Second agent> | |
|---|---|---|
| | Stearyl alcohol | 1.0 |
| | Cetanol | 4.0 |
| | POE(30) cetyl ether | 1.0 |
| | POE(2) cetyl ether | 0.5 |
| | Stearyl trimethyl ammonium chloride | 2.0 |
| | Vaseline | 2.0 |
| | Microcrystalline wax | 5.0 |
| | Phenoxyethanol | 0.2 |
| | Hydroxyethane diphosphonic acid | 0.2 |
| | Tetrasodium hydroxyethane diphosphonate | 0.3 |
| | Phosphoric acid | Amount to give pH3 |
| | 35% by mass Hydrogen peroxide | 15.0 |
| | Purified water | Balance |
| | Total | 100.0 |
| | Ratio of undiluted solution:propellant (nitrogen gas) | 95:5 |
| Eval-uations | Brightness | Very good |
| | Saturation | Very good |
| | Change of color tone | Very good |

As shown in Table 5, the present formulation also showed superior evaluation results in particular for the change of the color tone and the like as compared with the comparative example.

Formulation Example 4

In Formulation Example 4, a first agent in a gel emulsion state and a second agent in a liquid state of an oxidative hair dye composition were prepared. The first agent and the second agent each contained the components shown in Table 6. The first agent and the second agent shown in Example 12 of Table 6 were mixed with each other in a mass ratio of 1:1 to prepare an oxidative hair dye composition. Subsequent steps of the hair dyeing treatment were the same as those in Formulation Example 1. According to the methods shown in Formulation Example 1, the brightness, the saturation, and the change of the color tone were evaluated. The results are shown in Table 6. A comparative example different from Formulation Example 4 only in that resorcin was not mixed was also conducted (not shown).

TABLE 6

| | <First agent> | Example 12 |
|---|---|---|
| (A) | Resorcin | 0.05 |
| (C) | p-Phenylenediamine | 0.1 |
| (B) | m-Aminophenol | 0.1 |
| | 28% by mass Ammonia water | 4.0 |
| (D) | 70% by mass Monoethanolamine | 10.0 |
| | POE(3) oleyl ether phosphoric acid | 5.0 |
| | POE(3) alkyl(C12-14) ether | 10.0 |
| | Myristyl alcohol | 2.0 |
| | Isostearyl alcohol | 3.0 |
| | Glycerin | 3.0 |
| | Ammonium chloride | 0.1 |
| | Anhydrous sodium sulfite | 0.5 |
| | Sodium ethylenediamine hydroxylethyl triacetate | 0.5 |
| | Ascorbic acid | 0.5 |
| | Purified water | Balance |
| | Total | 100.0 |
| | <Second agent> | |
| | Stearyl alcohol | 2.0 |
| | POE(20) stearyl ether | 1.0 |

TABLE 6-continued

|  | | |
|---|---|---|
| | Stearyl trimethyl ammonium chloride | 0.5 |
| | Propylene glycol | 3.0 |
| | Diglycerin | 3.0 |
| | Phosphoric acid | Amount to give pH3 |
| | 35% by mass Hydrogen peroxide | 15.0 |
| | Purified water | Balance |
| | Total | 100.0 |
| Evaluations | Brightness | Very good |
| | Saturation | Very good |
| | Change of color tone | Very good |

As shown in Table 6, the present formulation also showed superior evaluation results in particular for the change of the color tone and the like as compared with the comparative example.

Formulation Example 5

In Formulation Example 5, a first agent in a gel state and a second agent in a liquid state of an oxidative hair dye composition were prepared. The first agent and the second agent each contained the components shown in Table 7. The first agent and the second agent shown in Example 13 of Table 7 were mixed with each other in a mass ratio of 1:1 to prepare an oxidative hair dye composition. Subsequent steps of the hair dyeing treatment were the same as those in Formulation Example 1. According to the methods shown in Formulation Example 1, the brightness, the saturation, and the change of the color tone were evaluated. The results thus obtained are shown in Table 7. A comparative example different from Formulation Example 5 only in that resorcin was not mixed was also conducted (data not shown).

TABLE 7

| | <First agent> | Example 13 |
|---|---|---|
| (A) | Resorcin | 0.05 |
| (C) | p-Phenylenediamine | 0.1 |
| (B) | m-Aminophenol | 0.1 |
| | 28% by mass Ammonia water | 4.0 |
| (D) | 70% by mass Monoethanolamine | 10.0 |
| | Myristyl alcohol | 2.0 |
| | Isostearyl alcohol | 3.0 |
| | Xanthan gum | 3.0 |
| | Glycerin | 3.0 |
| | Ammonium chloride | 0.1 |
| | Anhydrous sodium sulfite | 0.5 |
| | Sodium ethylenediamine hydroxyethyl triacetate | 0.5 |
| | Ascorbic acid | 0.5 |
| | Purified water | Balance |
| | Total | 100.0 |

| | <Second agent> | |
|---|---|---|
| | Stearyl alcohol | 2.0 |
| | POE(20) stearyl ether | 1.0 |
| | Stearyl trimethyl ammonium chloride | 0.5 |
| | Propylene glycol | 3.0 |
| | Diglycerin | 3.0 |
| | Phosphoric acid | Amount to give pH3 |
| | 35% by mass Hydrogen peroxide | 15.0 |
| | Purified water | Balance |
| | Total | 100.0 |
| Evaluations | Brightness | Very good |
| | Saturation | Very good |
| | Change of color tone | Very good |

As shown in Table 7, the present formulation also showed superior evaluation results in particular for the change of the color tone and the like as compared with the comparative example.

Formulation Example 6

In Formulation Example 6, a first agent in a liquid state and a second agent in a liquid state of an oxidative hair dye composition were prepared. The first agent and the second agent each contained the components shown in Table 8. The first agent and the second agent shown in Example 14 of Table 8 were mixed with each other in a mass ratio of 1:1 to prepare an oxidative hair dye composition. Subsequent steps of the hair dyeing treatment were the same as those in Formulation Example 1. According to the methods shown in Formulation Example 1, the brightness, the saturation, and the change of the color tone were evaluated. The results are shown in Table 8. A comparative example different from Formulation Example 6 only in that resorcin was not mixed was also conducted (data not shown)

TABLE 8

| | <First agent> | Example 14 |
|---|---|---|
| (A) | Resorcin | 0.05 |
| (C) | p-Phenylenediamine | 0.1 |
| (B) | m-Aminophenol | 0.1 |
| | 28% by mass Ammonia water | 4.0 |
| (D) | 70% by mass Monoethanolamine | 10.0 |
| | POE(6) oleyl ether | 20.0 |
| | Lauryl dimethyl amino acetate betaine | 5.0 |
| | Sodium lauryl sulfate | 5.0 |
| | Ethyl sulfuric acid lanolin fatty acid aminopropylethyl dimethylammonium | 0.5 |
| | Oleic acid | 10.0 |
| | Ethanol | 8.0 |
| | Polyethylene glycol 400 | 20.0 |
| | Sodium sulfite | 0.5 |
| | Disodium edetate | 0.5 |
| | Ascorbic acid | 0.5 |
| | Purified water | Balance |
| | Total | 100.0 |

| | <Second agent> | |
|---|---|---|
| | Cetanol | 2.0 |
| | Sodium lauryl sulfate | 0.5 |
| | Phosphoric acid | Amount to give pH3 |
| | Disodium edetate | 0.5 |
| | 35% by mass Hydrogen peroxide | 15.0 |
| | Purified water | Balance |
| | Total | 100.0 |
| Evaluations | Brightness | Very good |
| | Saturation | Very good |
| | Change of color tone | Very good |

As shown in Table 8, the present formulation also showed superior evaluation results in particular for the change of the color tone and the like as compared with the comparative example.

The foregoing embodiment and Examples are presented as exemplification for describing the present invention, and the present invention is not limited to the foregoing embodiment and Examples. For the embodiment disclosed for exemplification, various alternatives, alterations and modifications can be made without departing from the gist and scope of the present invention. For example, the subject of the present invention may possibly reside in features smaller in number than all the features of the particular disclosed embodiment. Accordingly, the scope of the claims of the invention is incorporated into the detailed description, and each of the claims itself claims a separate embodiment. The scope of the present invention is intended to include, in the scope of the claims, all of such alternative forms, alteration forms and modification forms, together with all the equivalents of these forms.

The invention claimed is:

1. A first agent for oxidative hair dye, comprising:
   an (A) component, which is at least one member selected from the group consisting of resorcin, derivatives thereof, and salts thereof, in a content not exceeding 0.15% by mass;
   a (B) component, which is at least one coupler selected from the group consisting of 5-amino-o-cresol, 5-(2-hydroxyethylamino)-2-methylphenol, derivatives thereof, and salts thereof;
   a (C) component, which is at least one dye intermediate selected from the group consisting of p-phenylenediamine, toluene-2,5-diamine, p-aminophenol, N,N-bis(2-hydroxyethyl)-p-phenylenediamine, derivatives thereof, and salts thereof, in a content between 0.01% by mass and 0.45% by mass;
   a (D) component, which is an alkanolamine; and
   ammonia,
   wherein the mass ratio of the content of the (B) component to the content of the (A) component in the first agent for oxidative hair dye is 0.5 to 15.

2. A method for stabilizing a color tone of an oxidative hair dye composition comprising a first agent for oxidative hair dye by improving storage stability of the hair dye composition, the method comprising forming the first agent for oxidative hair dye by mixing:
   an (A) component, which is at least one selected from the group consisting of resorcin, derivatives thereof, and salts thereof;
   a (B) component, which is at least one coupler selected from the group consisting of 5-amino-o-cresol, 5-(2-hydroxyethylamino)-2-methylphenol, derivatives thereof, and salts thereof;
   a (C) component, which is at least one dye intermediate selected from the group consisting of p-phenylenediamine, toluene-2,5-diamine, p-aminophenol, N,N-bis(2-hydroxyethyl)-p-phenylenediamine, derivatives thereof, and salts thereof;
   a (D) component, which is an alkanolamine; and
   ammonia,
   wherein the content of the (A) component is 0.15% by mass or less and the content of the (C) component is 0.01 to 0.45% by mass of the first agent for oxidative hair dye, and
   wherein the (A) component increases storage stability of the (B) component compared to the absence of the (A) component.

3. The first agent for oxidative hair dye according to claim 1, comprising 0.03 to 0.1% by mass of the (A) component.

4. The first agent for oxidative hair dye according to claim 1, wherein the content of the (D) component is 1.5% by mass or more.

5. The first agent for oxidative hair dye according to claim 1, wherein the mass ratio of the content of the (B) component to the content of the (A) component in the first agent for oxidative hair dye is 2 to 15.

6. A first agent for oxidative hair dye having improved storage stability comprising:
   (A) at least one member selected from the group consisting of resorcin, derivatives thereof, and salts thereof;
   (B) at least one coupler selected from the group consisting of in 5-amino-o-cresol, 5-(2-hydroxyethylamino)-2-methylphenol, derivatives thereof, and salts thereof;
   (C) at least one dye intermediate selected from the group consisting of p-phenylenediamine, toluene-2,5-diamine, p-aminophenol, N,N-bis(2-hydroxyethyl)-p-phenylenediamine, derivatives thereof, and salts thereof, in an amount between 0.01% by mass and 0.45% by mass;
   (D) an alkanolamine; and
   ammonia,
   wherein (A) is present in an amount effective for improving stability of (B) and up to 0.15% by mass, and
   a mass ratio of (A) to (B) is from 0.5 to 15.

7. The first agent for oxidative hair dye according to claim 6, comprising 0.01 to 0.15% by mass of (A).

* * * * *